(12) United States Patent
Hirota et al.

(10) Patent No.: US 10,178,941 B2
(45) Date of Patent: Jan. 15, 2019

(54) IMAGE PROCESSING APPARATUS, IMAGE PROCESSING METHOD, AND COMPUTER-READABLE RECORDING DEVICE

(71) Applicant: OLYMPUS CORPORATION, Tokyo (JP)

(72) Inventors: Masashi Hirota, Hachioji (JP); Yamato Kanda, Hino (JP); Makoto Kitamura, Hachioji (JP); Takashi Kono, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 1013 days.

(21) Appl. No.: 14/282,119

(22) Filed: May 20, 2014

(65) Prior Publication Data

US 2014/0257114 A1 Sep. 11, 2014

Related U.S. Application Data

(63) Continuation of application No. PCT/JP2012/080237, filed on Nov. 21, 2012.

(30) Foreign Application Priority Data

Nov. 25, 2011 (JP) .................................. 2011-258224

(51) Int. Cl.
*A61B 1/04* (2006.01)
*A61B 1/00* (2006.01)
(Continued)

(52) U.S. Cl.
CPC .......... *A61B 1/00009* (2013.01); *A61B 1/041* (2013.01); *A61B 5/0084* (2013.01);
(Continued)

(58) Field of Classification Search
CPC ................... G06T 7/0012; G06T 2207/10068
See application file for complete search history.

(56) References Cited

U.S. PATENT DOCUMENTS 8,295,566 B2 10/2012 Nishimura et al.
2007/0286469 A1 12/2007 Yamagata et al.
(Continued)

FOREIGN PATENT DOCUMENTS

CN 101404923 A 4/2009
EP 1 994 878 A1 11/2008
(Continued)

OTHER PUBLICATIONS

Partial Supplementary European Search Report dated Apr. 8, 2015 from related European Application No. 12 85 1696.0.
(Continued)

*Primary Examiner* — Michael D Abreu
(74) *Attorney, Agent, or Firm* — Scully, Scout, Murphy & Presser, P.C.

(57) ABSTRACT

An image processing apparatus includes an abnormal candidate region detection unit configured to detect an abnormal candidate region, as a candidate for an abnormal portion, from an intraluminal image obtained by capturing an image of an inside of a lumen of a subject, a tubular region detection unit configured to detect a tubular region from the intraluminal image, a connectivity determination unit configured to determine whether the abnormal candidate region and the tubular region are connected in a region of a color similar to that of the tubular region, and an abnormality determination unit configured to determine whether the abnormal candidate region is the abnormal portion, based on results of determination by the connectivity determination unit.

12 Claims, 13 Drawing Sheets

(51) Int. Cl.
*G06T 7/00* (2017.01)
*A61B 5/00* (2006.01)

(52) U.S. Cl.
CPC .......... *A61B 5/7282* (2013.01); *G06T 7/0012* (2013.01); *G06T 2207/10024* (2013.01); *G06T 2207/10068* (2013.01); *G06T 2207/30101* (2013.01)

(56) References Cited

U.S. PATENT DOCUMENTS

| | | | | |
|---|---|---|---|---|
| 2009/0074268 A1* | 3/2009 | Tanaka | ................ | G06T 7/0012 382/128 |
| 2009/0196495 A1 | 8/2009 | Inoue et al. | | |
| 2009/0208071 A1* | 8/2009 | Nishimura | ............ | A61B 1/041 382/128 |
| 2010/0316273 A1 | 12/2010 | Inoue et al. | | |

FOREIGN PATENT DOCUMENTS

| | | | |
|---|---|---|---|
| JP | 2002-291733 | A | 10/2002 |
| JP | 2006-304995 | A | 11/2006 |
| JP | 2008-012291 | A | 1/2008 |
| JP | 2009-066301 | A | 4/2009 |
| JP | 2009-273644 | A | 11/2009 |

OTHER PUBLICATIONS

International Search Report dated Mar. 5, 2013 issued in PCT/JP2012/080237.

* cited by examiner

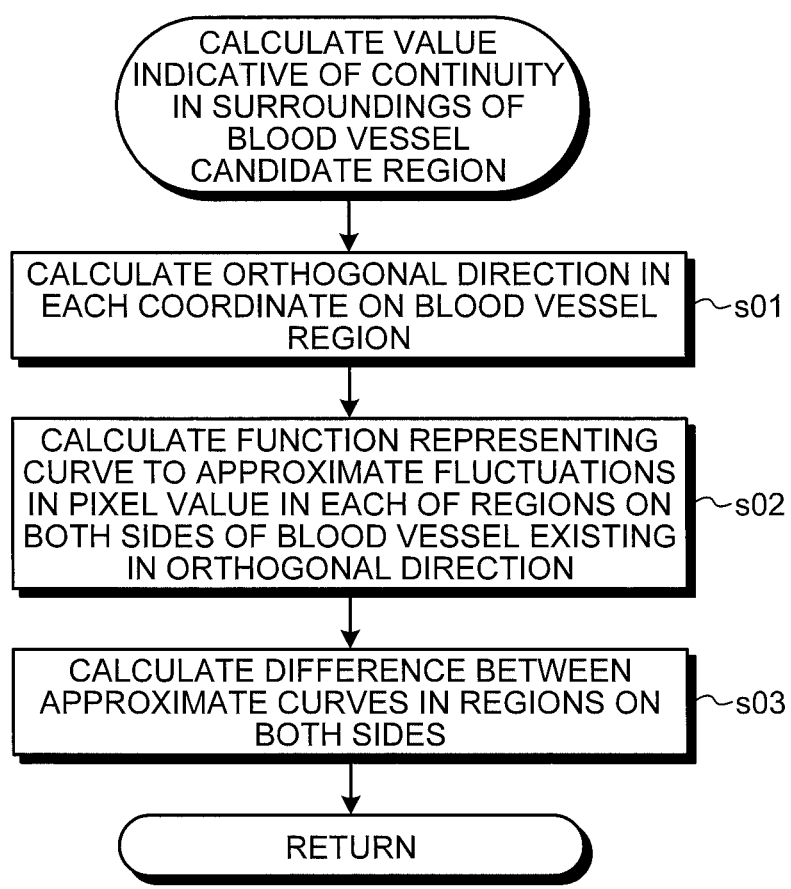

IMAGE PROCESSING APPARATUS, IMAGE PROCESSING METHOD, AND COMPUTER-READABLE RECORDING DEVICE

CROSS-REFERENCE TO RELATED APPLICATIONS

This application is a continuation of PCT international application Ser. No. PCT/JP2012/080237 filed on Nov. 21, 2012 which designates the United States, incorporated herein by reference, and which claims the benefit of priority from Japanese Patent Application No. 2011-258224, filed on Nov. 25, 2011, incorporated herein by reference.

BACKGROUND OF THE INVENTION

1. Field of the Invention

The present invention relates to an image processing apparatus, an image processing method, and a computer-readable recording device, for detecting an abnormal portion from a captured image of an inside of a subject.

2. Description of the Related Art

Conventionally, endoscopes have come into widespread use as a medical observation apparatus that is inserted into a subject such as a patient to observe the inside of the subject in a non-invasive manner. In recent years, there has been developed a swallowable endoscope (capsule endoscope) that houses an imaging device, a communication device, and the like in a capsule-shaped casing, and wirelessly transmits image data acquired through capturing an image by the imaging device to the outside of the subject.

However, a great deal of experience is required to conduct observations and diagnosis based on images of a lumen of the living body (intraluminal images) captured by these medical observation devices. Therefore, there is demand for a medical diagnosis supporting function to assist doctors in diagnosis.

As one of image recognition techniques for realizing the foregoing function, there has been proposed a technique for automatically detecting an abnormal portion from images to present images to be intensively examined for diagnosis. For example, Japanese Laid-open Patent Publication No. 2002-291733 discloses a method for properly detecting an abnormal portion by extracting a candidate for abnormal shadows and vascular shadows from lung regions in cross-sectional images and excluding overlapping portions between the candidate for abnormal shadows and the vascular shadows from the candidate for abnormal shadows.

SUMMARY OF THE INVENTION

In some embodiments, an image processing apparatus includes an abnormal candidate region detection unit configured to detect an abnormal candidate region, as a candidate for an abnormal portion, from an intraluminal image obtained by capturing an image of an inside of a lumen of a subject, a tubular region detection unit configured to detect a tubular region from the intraluminal image, a connectivity determination unit configured to determine whether the abnormal candidate region and the tubular region are connected in a region of a color similar to that of the tubular region, and an abnormality determination unit configured to determine whether the abnormal candidate region is the abnormal portion, based on results of determination by the connectivity determination unit.

In some embodiments, an image processing method includes detecting an abnormal candidate region, as a candidate for an abnormal portion, from an intraluminal image obtained by capturing an image of an inside of a lumen of a subject, detecting a tubular region from the intraluminal image, determining whether the abnormal candidate region and the tubular region are connected in a region of a color similar to that of the tubular region, and determining whether the abnormal candidate region is the abnormal portion, based on results of connectivity determination.

In some embodiments, a computer-readable recording device is a recording device with an executable program stored thereon. The program instructs a processor to perform detecting an abnormal candidate region, as a candidate for an abnormal portion, from an intraluminal image obtained by capturing an image of an inside of a lumen of a subject, detecting a tubular region from the intraluminal image, determining whether the abnormal candidate region and the tubular region are connected in a region of a color similar to that of the tubular region, and determining whether the abnormal candidate region is the abnormal portion, based on results of connectivity determination.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 5 is a flowchart of operation of a continuity determination unit illustrated in FIG. 1;

DETAILED DESCRIPTION OF THE PREFERRED EMBODIMENTS

Figure 1:
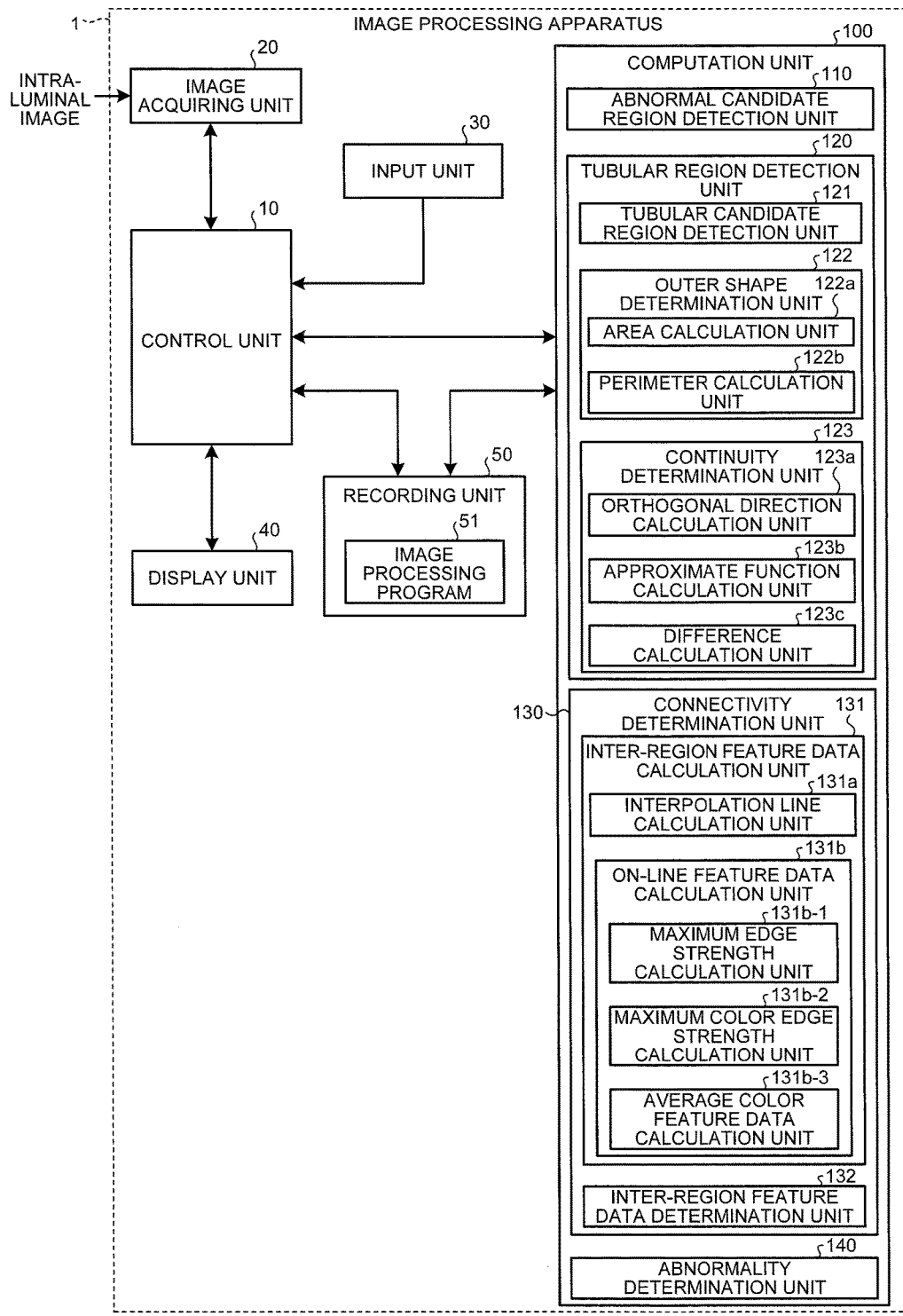
FIG. 1 is a block diagram illustrating a configuration of an image processing apparatus according to a first embodiment of the present invention.

An image processing apparatus, an image processing method, and a computer-readable recording device according to embodiments of the present invention will be described below with reference to the drawings. However, the present invention is not limited to these embodiments. In addition, the same reference numerals are used to refer to the same components throughout the drawings.

Described below as an example in relation to the embodiments is image processing by which an abnormal portion and a blood vessel region are differentiated from each other in an intraluminal image (hereinafter, referred to simply as image) acquired by capturing an image of the inside of a lumen of a subject by a medical observation device such as a capsule endoscope to detect the abnormal portion. In the foregoing embodiments, the intraluminal image to be target of the image processing is a color image with pixel levels (pixel values) for color components (wavelength components) of R (red), G (green), and B (blue) at respective pixel positions.

First Embodiment

FIG. 1 is a block diagram of a configuration of an image processing apparatus according to a first embodiment of the present invention. The image processing apparatus 1 illustrated in FIG. 1 includes: a control unit 10 that controls operation of the entire image processing apparatus 1; an image acquiring unit 20 that acquires image data corresponding to an image imaged by a medical observation device such as a capsule endoscope; an input unit 30 that accepts an input signal input from the outside; a display unit 40 that provides various displays; a recording unit 50 that stores the image data acquired by the image acquiring unit 20 and various programs; and a computation unit 100 that executes specified image processing on the image data.

The control unit 10 is realized by hardware such as a CPU. The control unit 10 reads various programs stored in the recording unit 50, transmits instructions to components constituting the image processing apparatus 1, and transfer data and others, according to image data input from the image acquiring unit 20 and operation signals input from the input unit 30, thereby to execute centralized control on operation of the entire image processing apparatus 1.

The image acquiring unit 20 is configured as appropriate according to the mode of the system including the medical observation device. For example, when the medical observation device is a capsule endoscope and a portable recording medium is used for exchange of image data with the medical observation device, the image acquiring unit 20 is configured as a reader that allows the recording medium to be detachably attached thereto and reads the image data of the stored intraluminal image. In addition, when a server is installed to save the image data of intraluminal images imaged by the medical observation device, the image acquiring unit 20 is configured as a communication device or the like connected to the server to conduct data communications with the server and acquire the image data of an intraluminal image. Alternatively, the image acquiring unit 20 may be configured as an interface device or the like that inputs an image signal via a cable from the medical observation device such as an endoscope.

The input unit 30 is realized by an input device such as a keyboard, a mouse, a touch panel, various switches, or the like, for example, which outputs accepted input signals to the control unit 10.

The display unit 40 is realized by a display device such as an LCD, an EL display, or the like, which displays various screens including the intraluminal images under control by the control unit 10.

The recording unit 50 is realized by various IC memories such as ROM or RAM including updatable flash memory, a hard disc built-in or connected via a data communication terminal, or an information recording device such as a CD-ROM and a reading device for the same. The recording unit 50 records image data of intraluminal images acquired by the image acquiring unit 20, programs for operating the image processing apparatus 1 and causing the image processing apparatus 1 to perform various functions, data to be used during execution of these programs, and the like. Specifically, the recording unit 50 records an image processing program 51 for causing the image processing apparatus 1 to execute image processing for detection of an abnormal portion from the intraluminal image.

The computation unit 100 is realized by hardware such as a CPU, which reads the image processing program 51 to execute image processing on image data corresponding to the intraluminal image, and performs various computational processes to detect an abnormal portion from the intraluminal image.

Next, a detailed configuration of the computation unit 100 will be described.

As illustrated in FIG. 1, the computation unit 100 includes: an abnormal candidate region detection unit 110 that detects from the image an abnormal candidate region as a candidate for an abnormal portion; a tubular region detection unit 120 that detects a tubular region from the image; a connectivity determination unit 130 that determines whether the abnormal candidate region and the tubular region are connected in a region of a color similar to that of the tubular region; and an abnormality determination unit 140 that determines whether the abnormal candidate region detected from the image is an abnormal portion, based on results of the determination by the connectivity determination unit 130. In the invention of the subject application, the region of a color similar to that of the tubular region refers to a region with color feature data in the vicinity of color feature data of the tubular region, more specifically, refers to a region in which the value of a specified wavelength component (for example, R component), amount of change in the specified wavelength component (edge strength), and specified color feature data (for example, G/R value), or amount of change in the specified color feature data (derivative value) falls within a range from the corresponding value of the tubular region.

Of the foregoing components, the tubular region detection unit 120 includes: a tubular candidate region detection unit 121 that detects a tubular candidate region as a candidate for the tubular region, based on the color feature data of each pixel in the image; an outer shape determination unit 122 that determines whether the tubular candidate region is a tubular region based on the outer shape of the tubular candidate region; and a continuity determination unit 123 that determines whether the tubular candidate region is the tubular region based on continuity of pixel values in a surrounding region of the tubular candidate region. More specifically, the outer shape determination unit 122 includes an area calculation unit 122a that calculates an area of the tubular candidate region and a perimeter calculation unit 122b that calculates the perimeter of the tubular candidate region. The continuity determination unit 123 includes an orthogonal direction calculation unit 123a that calculates a direction orthogonal to a longitudinal direction of the tubular candidate region in a plane of the image, an approximate function calculation unit 123b that calculates an approximate function to approximate changes in pixel values on both sides of the tubular candidate region in the orthogonal direction, and a difference calculation unit 123c that calculates a difference between the values of the approximate functions in the same coordinate in the orthogonal direction.

The connectivity determination unit 130 includes an inter-region feature data calculation unit 131 that calculates feature data in a region between the abnormal candidate region and the tubular region (hereinafter, referred to as inter-region feature data) and an inter-region feature data determination unit 132 that determines connectivity between the abnormal candidate region and the tubular region based on the inter-region feature data. More specifically, the inter-region feature data calculation unit 131 includes an interpolation line calculation unit 131a that calculates an interpolation line to interpolate between the abnormal candidate region and the tubular region, and an on-line feature data calculation unit 131b that calculates feature data on the interpolation line. Of the foregoing components, the on-line feature data calculation unit 131b includes a maximum edge strength calculation unit 131b-1, a maximum color edge strength calculation unit 131b-2, and an average color feature data calculation unit 131b-3. The maximum edge strength calculation unit 131b-1 calculates an edge strength on the interpolation line, that is, a maximum value of changes in pixel values (derivative values) between adjacent pixels or pixels at specified intervals therebetween on the interpolation line. The maximum color edge strength calculation unit 131b-2 calculates a color edge strength on the interpolation line, that is, a maximum value of changes in color feature data (derivative values) between adjacent pixels or pixels at specified intervals therebetween on the interpolation line. The average color feature data calculation unit 131b-3 calculates an average value of the color feature data on the interpolation line.

Figure 2:
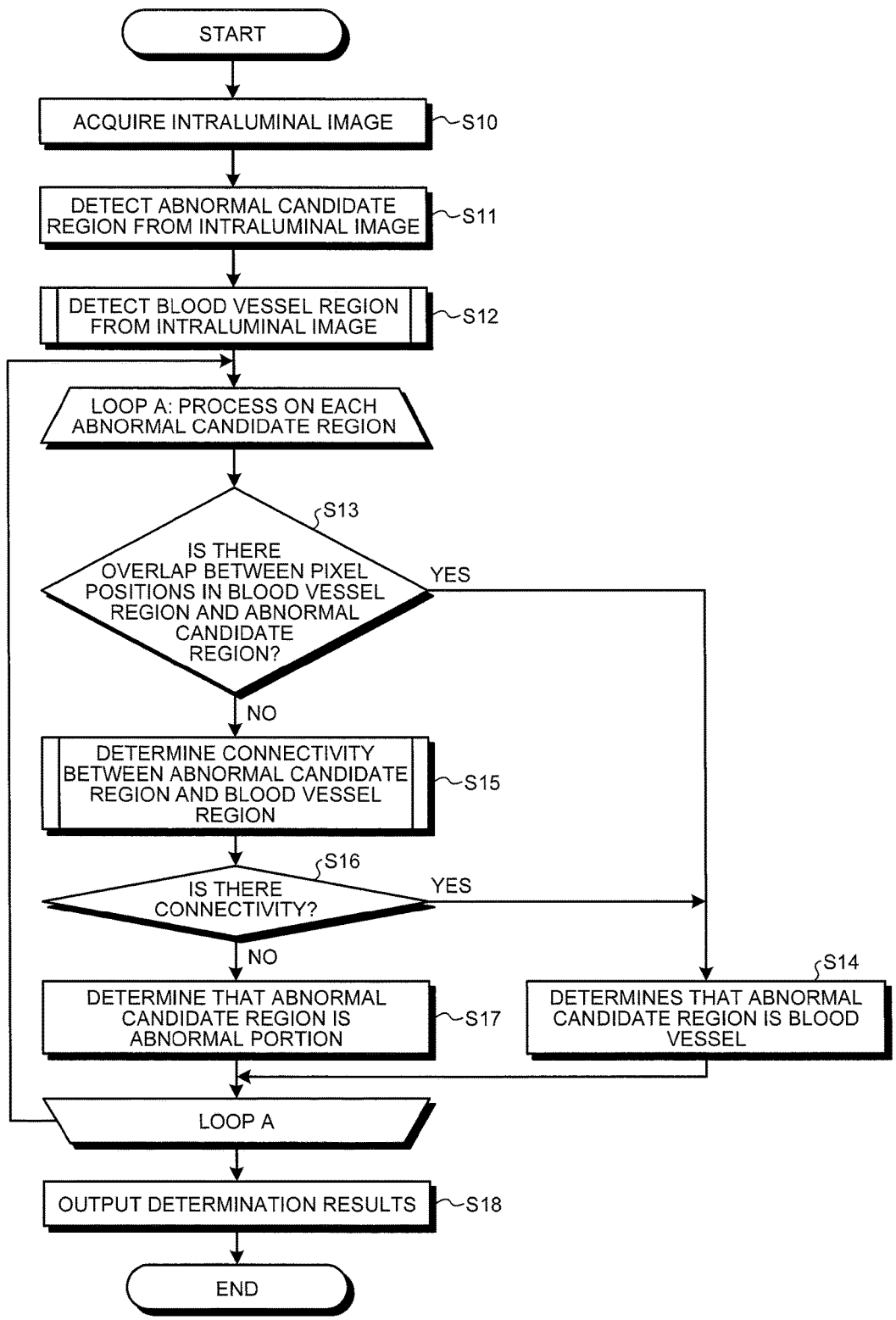
FIG. 2 is a flowchart of operation of the image processing apparatus illustrated in FIG. 1.
Figure 3:
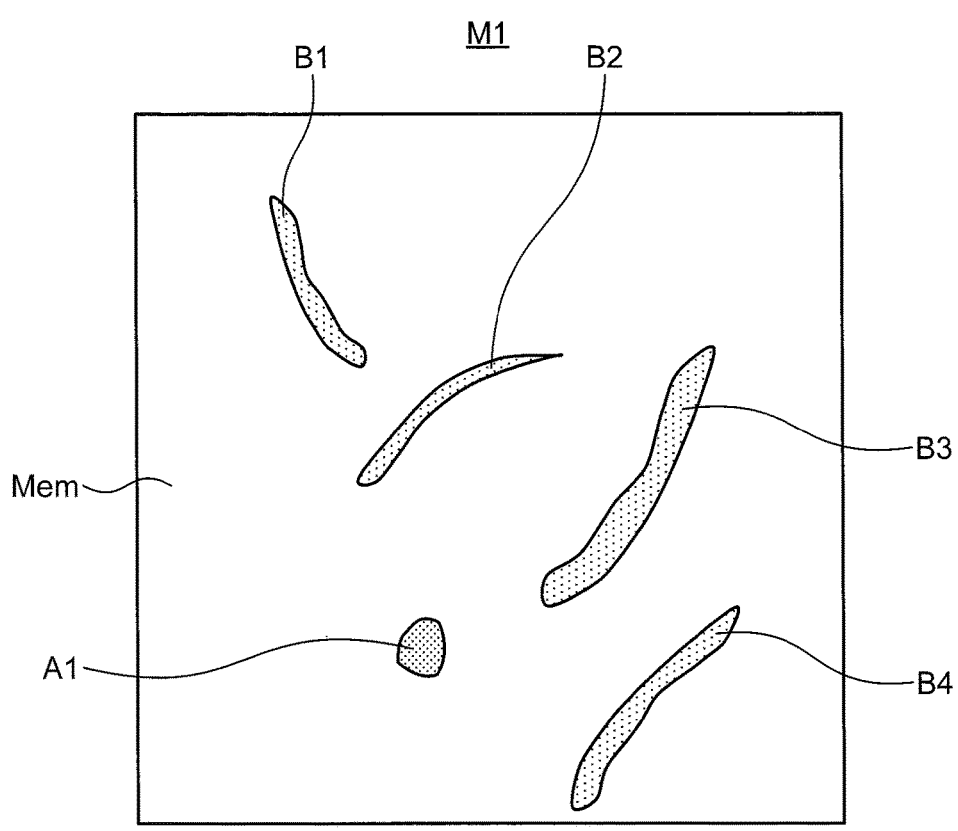
FIG. 3 is a schematic view of one example of an image to be processed by the image processing apparatus illustrated in FIG. 1.

Next, operation of the image processing apparatus 1 will be described. FIG. 2 is a flowchart of operation of the image processing apparatus 1. FIG. 3 is a schematic view of one example of an image to be processed by the image processing apparatus 1. As illustrated in FIG. 3, seen in an image M1 are a mucous membrane Mem, a region A1 different in state from the surrounding mucous membrane, and long and thin tubular regions B1 to B4.

Firstly, at step S10, the image acquiring unit 20 acquires an intraluminal image of a subject and stores the same in the recording unit 50. The computation unit 100 reads sequentially an image to be processed (for example, image M1) from the recording unit 50.

At step S11, the abnormal candidate region detection unit 110 detects an abnormal candidate region from the image. Various known methods can be used to detect the abnormal candidate region. For example, pixel values of pixels of the image are mapped to a feature space based on color information of the pixels, and are subjected to clustering in the feature space. Then, normal mucous membrane clusters and abnormal portion clusters are identified based on information such as the positions of the clusters and the average values of the clusters (that is, barycentric coordinates), thereby to detect a candidate region for an abnormal portion (for example, refer to Japanese Laid-open Patent Publication No. 2005-192880).

Figure 4:
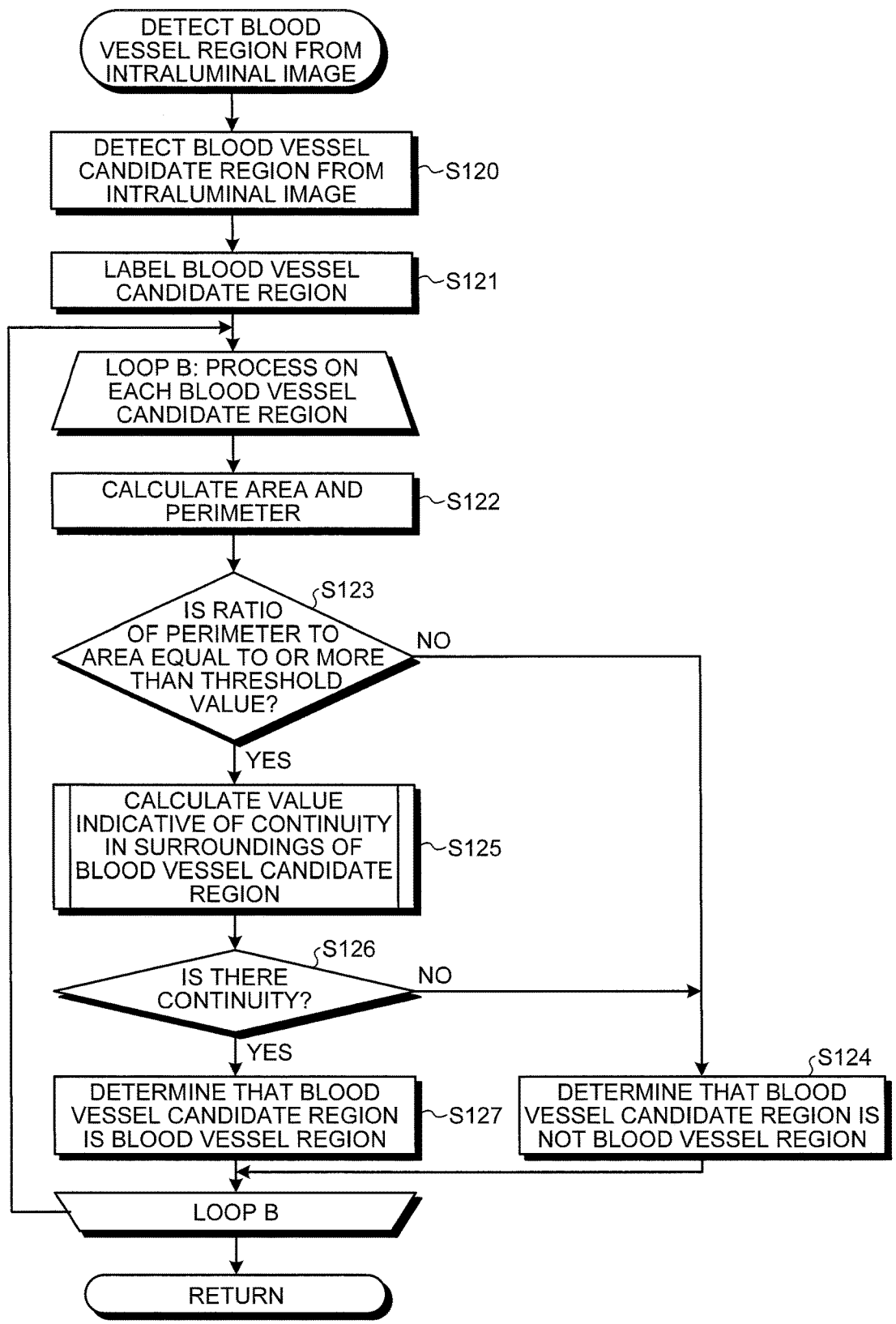
FIG. 4 is a flowchart of detailed operation of a tubular region detection unit illustrated in FIG. 1.

At subsequent step S12, the tubular region detection unit 120 detects a blood vessel candidate region from the image, and determines whether the blood vessel candidate region is a blood vessel region based on the shape of the blood vessel candidate region and the continuity of changes in the pixel values in a surrounding region of the blood vessel candidate region, thereby to detect the blood vessel region. Various known method can be used to detect the blood vessel candidate region. In the first embodiment, the blood vessel candidate region is detected by the method described below. FIG. 4 is a flowchart of detailed operation of the tubular region detection unit 120 at step S12.

First, at step S120, the tubular candidate region detection unit 121 detects blood vessel candidate regions from the image. Specifically, the tubular candidate region detection unit 121 executes template matching using a template for blood vessel model, and extracts structural components based on results of the matching (for example, refer to Japanese Laid-open Patent Publication No. 2004-181096).

At subsequent step S121, the tubular candidate region detection unit 121 performs a labeling process on the detected blood vessel candidate regions. Then, the tubular candidate region detection unit 121 performs a process of loop B on each of the blood vessel candidate regions to determine whether the blood vessel candidate region is a blood vessel region.

Specifically, at step S122, the outer shape determination unit 122 causes the area calculation unit 122a to calculate an area A of the blood vessel candidate region, and causes the perimeter calculation unit 122b to calculate a perimeter L of the blood vessel candidate region. Then, at step S123, the outer shape determination unit 122 calculates a ratio L/A of the area A to the perimeter L, and determines whether the ratio L/A is equal to or more than a specified threshold value.

The process at step S123 is equivalent to a process for determining whether the outer shape of the blood vessel candidate region is tubular, and is performed to exclude non-tubular regions such as rubors. Therefore, any other method can be used to determine whether the outer shape is tubular. For example, it may be determined whether the outer shape of the blood vessel candidate region is tubular by comparing a ratio L1/L2 between values L1 and L2 (L1>L2) calculated by the following equations (1) and (2) with a specified threshold value.

$$L1 \times L2 = A \tag{1}$$

$$2(L1+L2) = L \tag{2}$$

When it is determined as a result of the determination at step S123 that the ratio L/A is smaller than the threshold value (step S123: No), the outer shape determination unit 122 determines that the blood vessel candidate region is not a blood vessel region (step S124).

Figure 6A:
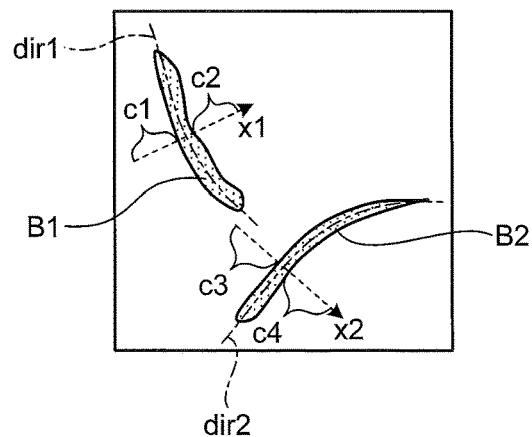
FIG. 6A is a diagram for describing a process performed by the continuity determination unit illustrated in FIG. 1.
Figure 6B:
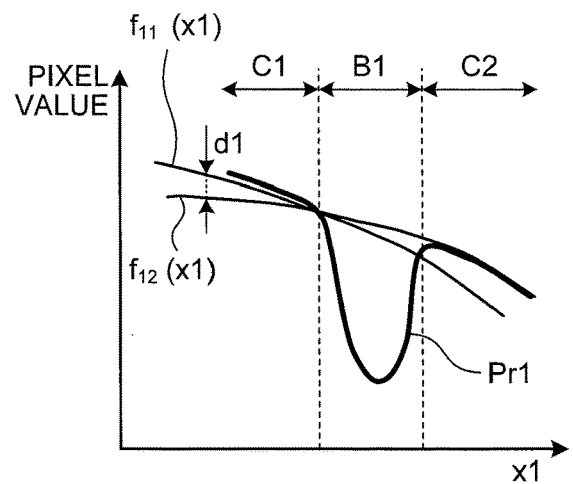
FIG. 6B is a diagram for describing a process performed by the continuity determination unit illustrated in FIG. 1.
Figure 6C:
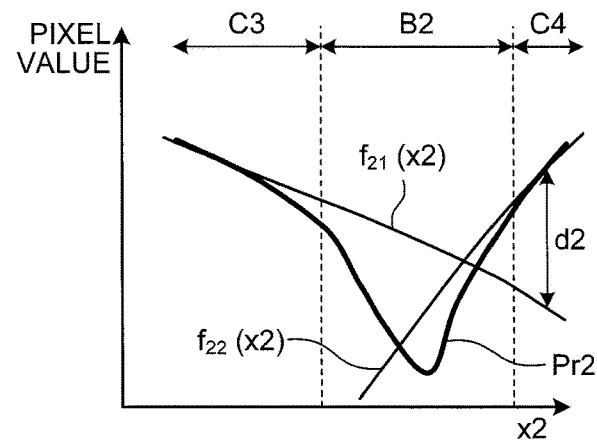
FIG. 6C is a diagram for describing a process performed by the continuity determination unit illustrated in FIG. 1.

Meanwhile, it is determined that the ratio L/A is equal to or more than the threshold value (step S123: Yes), the continuity determination unit 123 further calculates a value indicative of continuity of pixel values surrounding the blood vessel candidate region (step S125). More specifically, the continuity determination unit 123 calculates a value indicative of whether there are continuous changes in the pixel values in the mucous membrane regions on both sides of the blood vessel candidate region. FIG. 5 is a flowchart of detailed operation of the continuity determination unit 123 at step S125. FIGS. 6A to 6C are diagrams for describing a process performed by the continuity determination unit 123. Of the foregoing diagrams, FIG. 6A corresponds to a part of the image M1 illustrated in FIG. 3.

At step s01, the orthogonal direction calculation unit 123*a* calculates a direction orthogonal to the longitudinal direction of the blood vessel candidate region in the plane of the image. The orthogonal direction here can be calculated as a direction of a second eigenvector of a Hessian matrix in each of the pixels on the blood vessel candidate region. The Hessian matrix is given by the following expression (3) using a pixel value I of a pixel in position coordinates (x, y).

$$\begin{pmatrix} \frac{\partial^2 I}{\partial x^2} & \frac{\partial^2 I}{\partial x \partial y} \\ \frac{\partial^2 I}{\partial x \partial y} & \frac{\partial^2 I}{\partial y^2} \end{pmatrix} \quad (3)$$

In the first embodiment, R value of each pixel is used as pixel value I. Accordingly, in the case of FIG. 6A, for example, orthogonal directions x1 and x2 are calculated with respect to longitudinal directions dir1 and dir2 of blood vessel regions B1 and B2, respectively.

At step s02, the approximate function calculation unit 123*b* calculates a function representing a curve to approximate fluctuations in pixel value on the both sides of the blood vessel candidate region, in the orthogonal direction with respect to the longitudinal direction of the blood vessel candidate region. For example, in the case of the blood vessel candidate region B1 illustrated in FIG. 6A, functions $f_{11}(x1)$ and $f_{12}(x1)$ of approximate curves are calculated to approximate pixel value profile Pr1 in regions C1 and C2 on the both sides of the blood vessel candidate region B1 to pixel value profile Pr1 in the orthogonal direction x1, as illustrated in FIG. 6B. In addition, in the case of the blood vessel candidate region B2 illustrated in FIG. 6A, functions $f_{21}(x2)$ and $f_{22}(x2)$ of approximate curves are calculated to approximate pixel value profile Pr2 in regions C3 and C4 on the both sides of the blood vessel candidate region B2 to pixel value profile Pr2 in the orthogonal direction x2, as illustrated in FIG. 6C.

At step s03, the difference calculation unit 123*c* substitutes coordinates of a plurality of points in the orthogonal direction to the two functions of approximate curves on the both sides of the blood vessel candidate region, thereby to calculate differential values between the both approximate curves. Then, the difference calculation unit 123*c* sums up these differential values and divides the summed value by the number of coordinates at which the differential values are calculated, thereby to perform normalization. For example, in the case of the blood vessel candidate region B1, a differential value $d1=f_{11}(x1)-f_{12}(x1)$ is calculated at each pixel on an x1 axis in the region C1, and the summed value of the differential values d1 is divided by the number of pixels on the x1 axis in the region C1. This matter also applies to the region C2. In the case of the blood vessel candidate region B2, a differential value $d2=f_{21}(x2)-f_{22}(x2)$ at each pixel on an x2 axis is calculated in each of the regions C3 and C4, and the summed value of the differential values d2 is divided by the number of pixels on the x2 axis. By performing such normalization, it is possible to obtain a differential value not depending on the number of coordinates (number of pixels) in each of the regions. After that, the computation unit 100 returns operation to a main routine.

At step S126, the continuity determination unit 123 compares the thus calculated differential value with a specified threshold value to determine continuity between the regions surrounding the blood vessel candidate region. Specifically, when the differential value is smaller than the specified threshold value (for example, the differential value d1 is small as illustrated in FIG. 6B), the continuity determination unit 123 determines that there is continuity between the regions on the both sides of the blood vessel candidate region. Meanwhile, when the differential value is larger than the specified threshold value (for example, the differential value d2 is large as illustrated in FIG. 6C), the continuity determination unit 123 determines that there is no continuity between the regions on the both sides of the blood vessel candidate region.

When it is determined that there is continuity between the regions surrounding the blood vessel candidate region (step S126: Yes), the tubular region detection unit 120 determines that the tubular candidate region is a blood vessel region (step S127). Meanwhile, it is determined that there is no continuity between the regions surrounding the blood vessel candidate region (step S126: No), the tubular region detection unit 120 determines that the tubular candidate region is not a blood vessel region (step S124).

Accordingly, it is possible to include blood vessel candidate regions having a pixel value profile with a depression resulting from a difference in light absorption characteristics, such as a blood vessel, (for example, the blood vessel candidate region B1 having the pixel value profile Pr1) in the category of blood vessel regions, and exclude blood vessel candidate regions having a pixel value profile resulting from a structure of a groove existing between mucous membranes (for example, the blood vessel candidate region B2 having the pixel value profile Pr2) from the category of blood vessel regions. After that, operation of the computation unit 100 returns to the main routine.

After step S12, the computation unit 100 executes a process of loop A on each of the abnormal candidate regions.

First, at step S13, the connectivity determination unit 130 determines based on the coordinate value of the abnormal candidate region detected at step S11 and the coordinate value of the blood vessel region detected at step S12, whether the two regions overlap (that is, at least some of their pixel positions overlap). When the pixel positions overlap (step S13: Yes), the abnormality determination unit 140 determines that the abnormal candidate region is a blood vessel (step S14).

Figure 7:
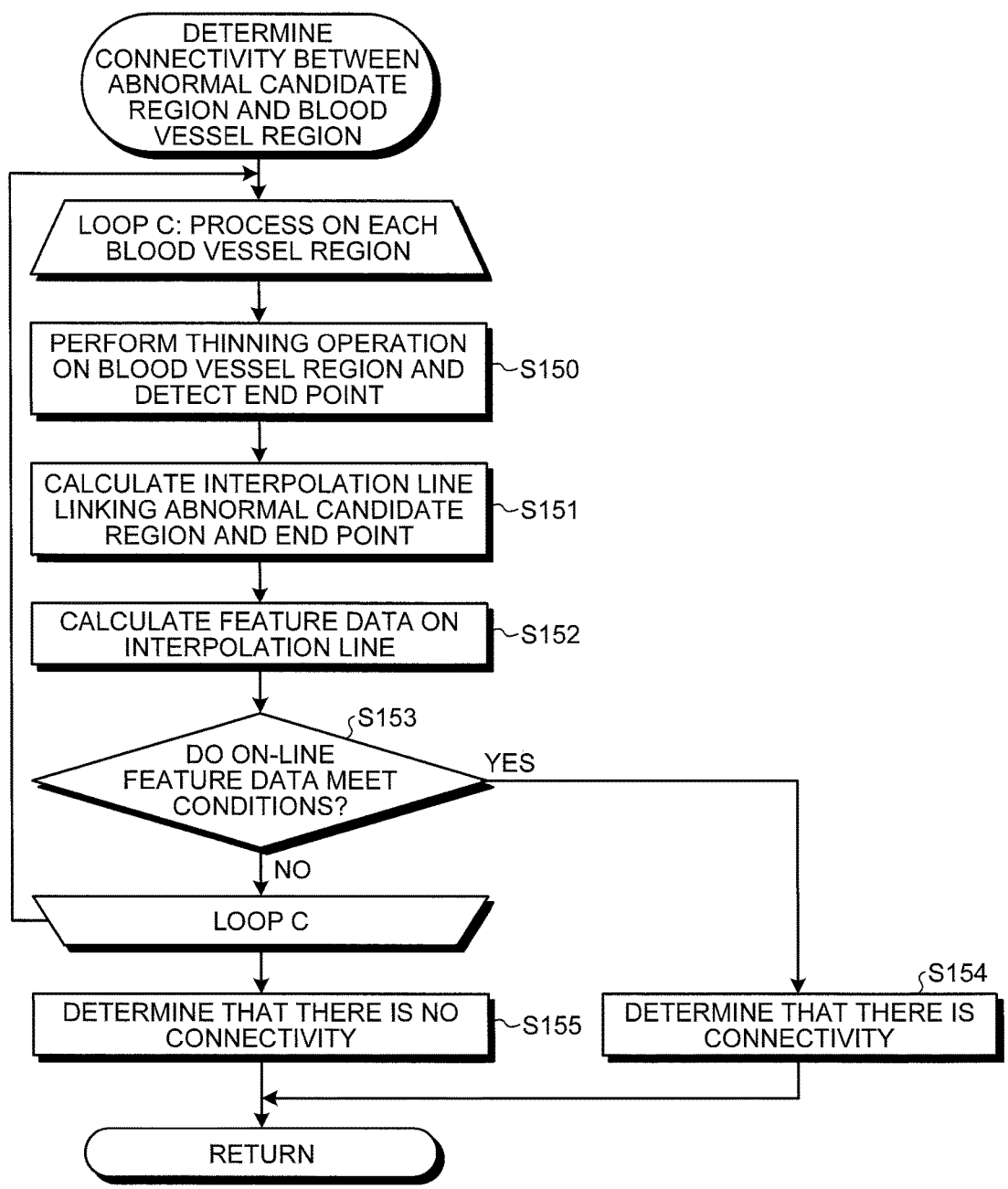
FIG. 7 is a flowchart of operation of a connectivity determination unit illustrated in FIG. 1.
Figure 8A:
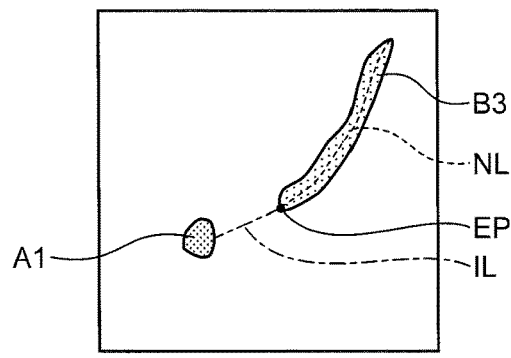
FIG. 8A is a diagram for describing a process performed by the connectivity determination unit illustrated in FIG. 1.
Figure 8B:
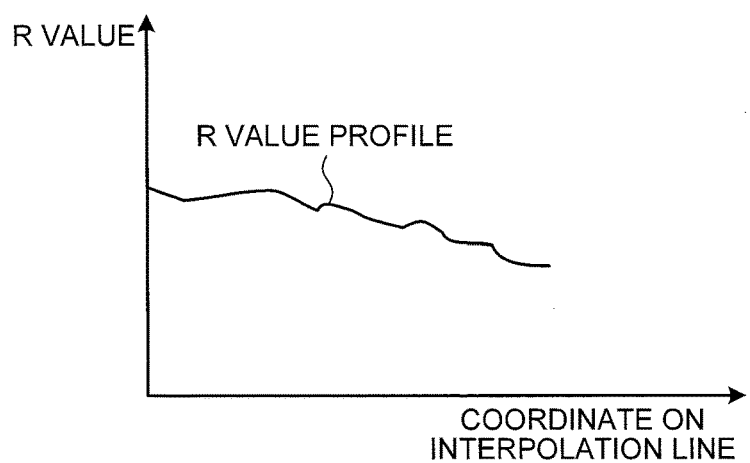
FIG. 8B is a diagram for describing a process performed by the connectivity determination unit illustrated in FIG. 1.
Figure 8C:
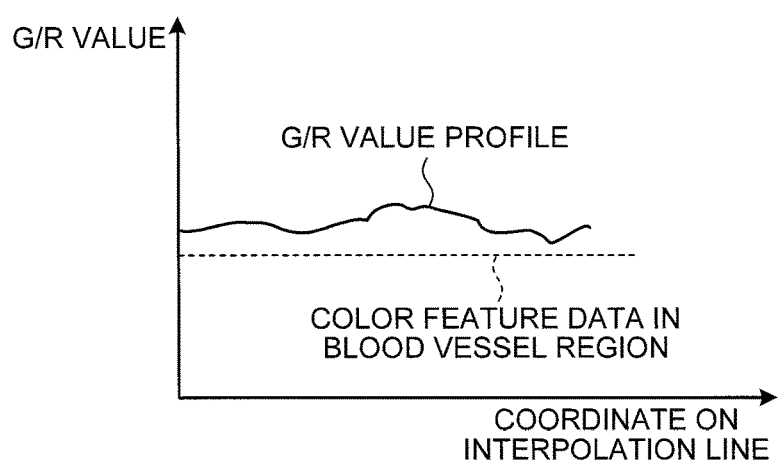
FIG. 8C is a diagram for describing a process performed by the connectivity determination unit illustrated in FIG. 1.

Meanwhile, when the pixel positions do not overlap (step S13: No), the connectivity determination unit 130 determines on the presence or absence of connectivity between the abnormal candidate region and the blood region at subsequent step S15. Specifically, the connectivity determination unit 130 determines whether the two regions are connected by a region of a color similar to that of the blood vessel region, based on the feature data of the region between the abnormal candidate region and the blood vessel region (inter-region feature data). FIG. 7 is a flowchart of detailed operation of the connectivity determination unit 130 at step S15. FIGS. 8A to 8C are diagrams for describing a process performed by the connectivity determination unit 130. Of the foregoing diagrams, FIG. 8A corresponds to a part of the image M1 illustrated in FIG. 3.

First, the connectivity determination unit 130 performs a process of loop C on each of the blood vessel regions. Specifically, at step S150, the interpolation line calculation unit 131*a* performs thinning operation on the blood vessel region to detect an end point (refer to CG-ARTS Society, "Digital Image Processing," pp. 185 to 189). For example, in the case of FIG. 8A, an end point EP of a line NL obtained by thinning a blood vessel region B3.

At subsequent step S151, the interpolation line calculation unit 131*a* calculates an interpolation line linking the abnormal candidate region and the end point. In FIG. 8A, an interpolation line IL linking the end point EP and the abnormal candidate region A1 is calculated. In FIG. 8A, the interpolation line is straight as an example. Alternatively, the interpolation line may be calculated by another method so as to be straight or curved as far as the interpolation line is capable of interpolation between the abnormal candidate region and the blood vessel region. For example, the interpolation line may be formed by sampling in sequence some points from the blood vessel region beginning at the end point EP along a line NL, and then linking the sampled points and the gravity center of the abnormal candidate region to draw a spline curve.

At step S152, the on-line feature data calculation unit 131b calculates maximum edge strength, maximum color edge strength, and average color feature data as feature data on the interpolation line (on-line feature data). Specifically, the on-line feature data calculation unit 131b calculates the maximum value of derivative value of R value on the interpolation line as maximum edge strength, calculates the maximum value of derivative value of G/R value as maximum color edge strength, and calculates the average value of G/R value as average color feature data.

At step S153, the inter-region feature data determination unit 132 determines whether the foregoing three on-line feature data meet the following three conditions:

Condition 1: The maximum edge strength is equal to or less than a specified threshold value;

Condition 2: The maximum color edge strength is equal to or less than a specified threshold value; and Condition 3: A difference between the average color feature data and the average color feature data in the blood vessel region is equal to or less than a specified threshold value.

The state in which there is connectivity between the abnormal candidate region and the blood vessel region here refers to the state in which there is no structural discontinuity such as a groove between the two regions, and the two regions are connected in a color similar to that of the blood vessel region without sharp color change. In this case, as illustrated in FIG. 8B, a pixel value (R value) profile on the interpolation line linking the two regions gently changes (meeting the foregoing condition 1). In addition, as illustrated in FIG. 8C, a color feature data (G/R value) profile on the interpolation line gently changes (meeting the foregoing condition 2) in the vicinity of the color feature data in the blood vessel region (meeting the foregoing condition 3). Therefore, by comparing the feature data on the interpolation line with the foregoing conditions 1 to 3, it is possible to determine connectivity between the abnormal candidate region and the blood vessel region.

When the on-line feature data meet all of the foregoing conditions 1 to 3 (step S153: Yes), the connectivity determination unit 130 exits from the loop C and determines that the abnormal candidate region has connectivity with the blood vessel region (step S154). Meanwhile, when the on-line feature data do not meet at least one of the foregoing conditions 1 to 3 (step S153: No), the connectivity determination unit 130 repeats the process of loop C on another blood vessel region as a target of determination. Then, when the process is completely performed on all of the blood vessel regions, if no blood vessel region meeting all of the foregoing conditions 1 to 3 is detected, the connectivity determination unit 130 determines that the abnormal candidate region has no connectivity with the blood vessel region (step S155). After that, the computation unit 100 returns operation to the main routine.

At step S16 after step S15, the abnormality determination unit 140 performs determination on the abnormal candidate region based on results of the determination by the connectivity determination unit 130. Specifically, when it is determined that the abnormal candidate region has connectivity with the blood vessel region (step S16: Yes), the abnormality determination unit 140 determines that the abnormal candidate region is blood vessels (a region with dense blood vessels), not an abnormal portion (step S14). Meanwhile, when it is determined that the abnormal candidate region has no connectivity with the blood vessel region (step S16: No), the abnormality determination unit 140 determines that the abnormal candidate region is an abnormal portion (step S17).

After performing the foregoing determination process on all of the abnormal candidate regions detected at step S11, the computation unit 100 exits from the loop A and outputs results of the determination on abnormal portion (step S18). Accordingly, the control unit 10 records the results of the determination on abnormal portion in the recording unit 50. At that time, the control unit 10 may display the results of the determination on abnormal portion on the display unit 40 or the like. After that, the image processing apparatus 1 terminates the process.

As described above, according to the first embodiment, it is determined whether an abnormal candidate region detected from an image is an abnormal portion by determining connectivity between the abnormal candidate region and the tubular blood vessel region, which makes it possible to differentiate between the abnormal portion and the blood vessels and properly detect the abnormal portion.

In the first embodiment, to detect a blood vessel region, determination is made on a blood vessel candidate region detected from an image based on the outer shape of the region, and then determination on connectivity between the blood vessel candidate region and its surrounding region. Alternatively, it may be determined whether the blood vessel candidate region is a blood vessel region by determining directly continuity between the blood vessel candidate region and its surrounding region.

Modification

Next, a modification of the first embodiment will be described.

Figure 9:
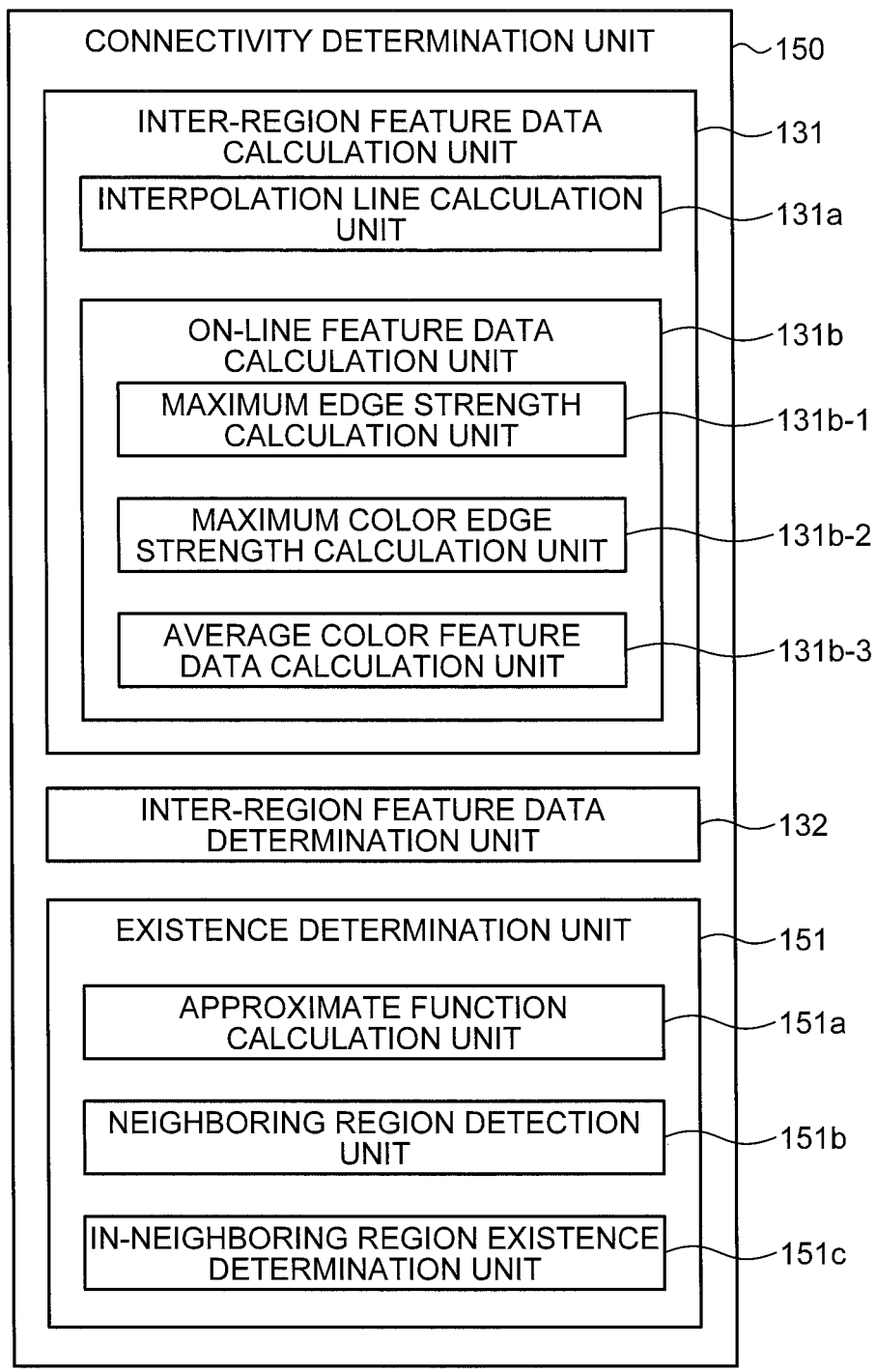
FIG. 9 is a block diagram illustrating a configuration of a connectivity determination unit in a modified example of the first embodiment.

An image processing apparatus according to the modified example includes a connectivity determination unit 150 illustrated in FIG. 9, instead of the connectivity determination unit 130 illustrated in FIG. 1. The components of the image processing apparatus other than the connectivity determination unit 150 are the same as those illustrated in FIG. 1.

As illustrated in FIG. 9, in addition to the inter-region feature data calculation unit 131 and the inter-region feature data determination unit 132, the connectivity determination unit 150 further has an existence determination unit 151 that determines whether an abnormal candidate region exists in a direction further extended from the longitudinal direction of a blood vessel region (hereinafter, referred to simply as extending direction of the blood vessel region) to determine connectivity between the abnormal candidate region and the blood vessel region, based on relative positional relationship between the abnormal candidate region and the blood vessel region.

More specifically, the existence determination unit 151 includes an approximate function calculation unit 151a that calculates a function approximating the shape of a blood vessel region (approximate function), a neighboring region detection unit 151b that detects in an image a neighboring region within a specified distance from the approximate function, and an in-neighboring region existence determination unit 151c that determines whether an abnormal candidate region exists in the neighboring region.

A region in which a plurality of blood vessels crosses under mucous membranes may be detected as an abnormal candidate region due to its non-tubular outer shape. It is considered that such abnormal candidate regions exist in the extending direction of the blood vessel region. Thus, in the modified example, to determine connectivity between the abnormal candidate region and the blood vessel region (step S15 of FIG. 2), it is determined whether the abnormal candidate region exists in the extending direction of the blood vessel region, and only when the abnormal candidate region exists in the extending direction, connectivity determination is made using the feature data on the interpolation line.

Figure 10:
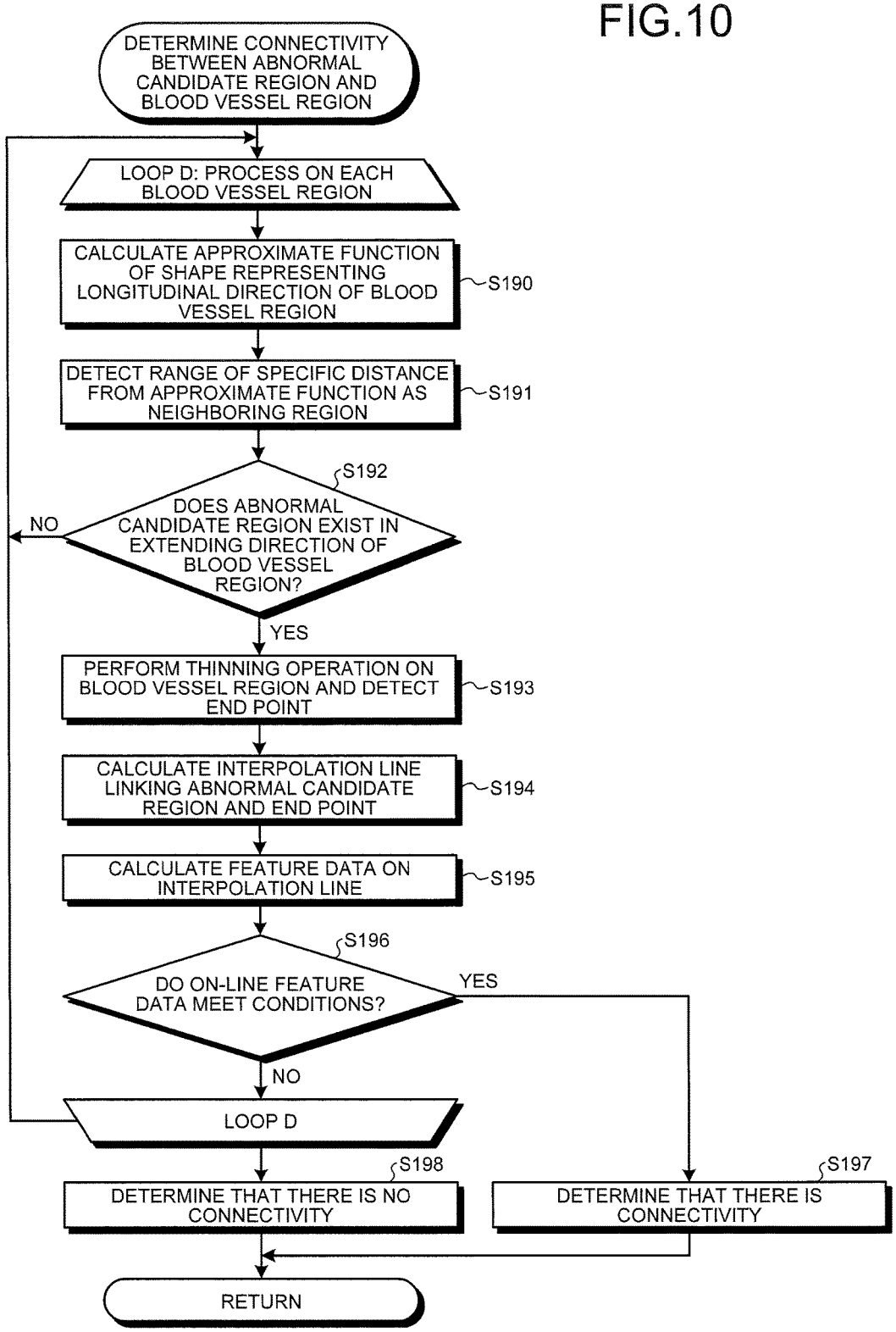
FIG. 10 is a flowchart of operation of the connectivity determination unit illustrated in FIG. 9.
Figure 11:
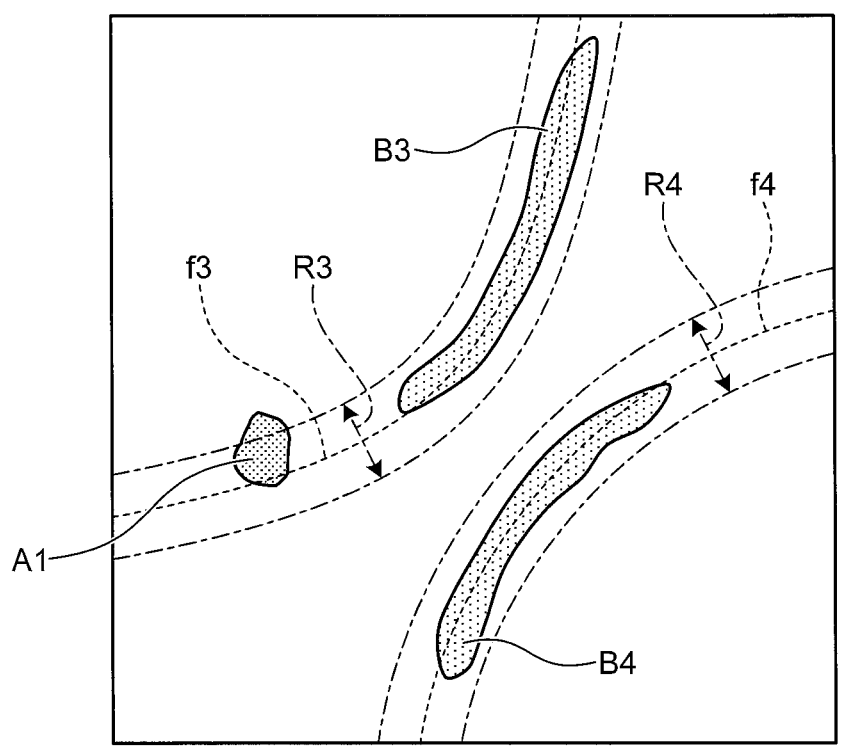
FIG. 11 is a schematic view for describing a process performed by the connectivity determination unit illustrated in FIG. 9.

FIG. 10 is a flowchart of operation of the connectivity determination unit 150 in the modified example. FIG. 11 is a schematic view for describing a process performed by the connectivity determination unit 150, which corresponds to a part of the image M1 illustrated in FIG. 3.

The connectivity determination unit 150 first performs a loop D process on each of the blood vessel regions detected from the intraluminal image. Specifically, at step S190, the approximate function calculation unit 151a calculates a function of position coordinates approximating the shape of the blood vessel region in the longitudinal direction (approximate function). To calculate the approximate function, for example, the position coordinates (x, y) of each pixel in the image may be used to calculate the coefficient of quadratic function given by the following equation (4) by least-square method.

$$y = ax^2 + bx + c \quad (4)$$

In the case of FIG. 11, for example, a function f3 approximating the shape of the blood vessel region B3 in the longitudinal direction and a function f4 approximating the shape of the blood vessel region B4 in the longitudinal direction are calculated.

At subsequent step S191, the neighboring region detection unit 151b detects a region within a specific distance from the approximate function in the intraluminal image, as a neighboring region. The neighboring region can be detected by generating a distance image in which a pixel value of each pixel in the image is converted to a distance from the pixel position on the approximate function, and extracting a region with a pixel value equal to or less than a specified threshold value (that is, a region in a distance of the threshold value or less) from the distance image. In the case of FIG. 11, for example, a neighboring region R3 of the function f3 and a neighboring region R4 of the function f4 are detected.

At step S192, the in-neighboring region existence determination unit 151c determines whether an abnormal candidate region exists in the neighboring region, that is, whether an abnormal candidate region exists in the extending direction of the blood vessel region. In the case of FIG. 11, for example, since a part of the abnormal candidate region A1 overlaps the neighboring region R3, the in-neighboring region existence determination unit 151c determines that the abnormal candidate region exists in the extending direction of the blood vessel region R3. Meanwhile, since no abnormal candidate region exists in the neighboring region R4, the in-neighboring region existence determination unit 151c determines that no abnormal candidate region exists in the extending direction of the blood vessel region B4.

When no abnormal candidate region exists in the extending direction of the blood vessel region (step S192: No), the connectivity determination unit 150 moves operation to the process on a next blood vessel region. Meanwhile, when an abnormal candidate region exists in the extending direction of the blood vessel region (step S192: Yes), the connectivity determination unit 150 moves operation to step S193. Steps S193 to S198 illustrated in FIG. 10 correspond to steps S150 to S155 illustrated in FIG. 7.

As described above, according to the modified example, only when an abnormal candidate region exists in the extending direction of the blood vessel region, determination is made on connectivity between the abnormal candidate region and the blood vessel region, which makes it possible to reduce the amount of calculation for connectivity determination.

Second Embodiment

Next, a second embodiment of the present invention will be described.

Figure 12:
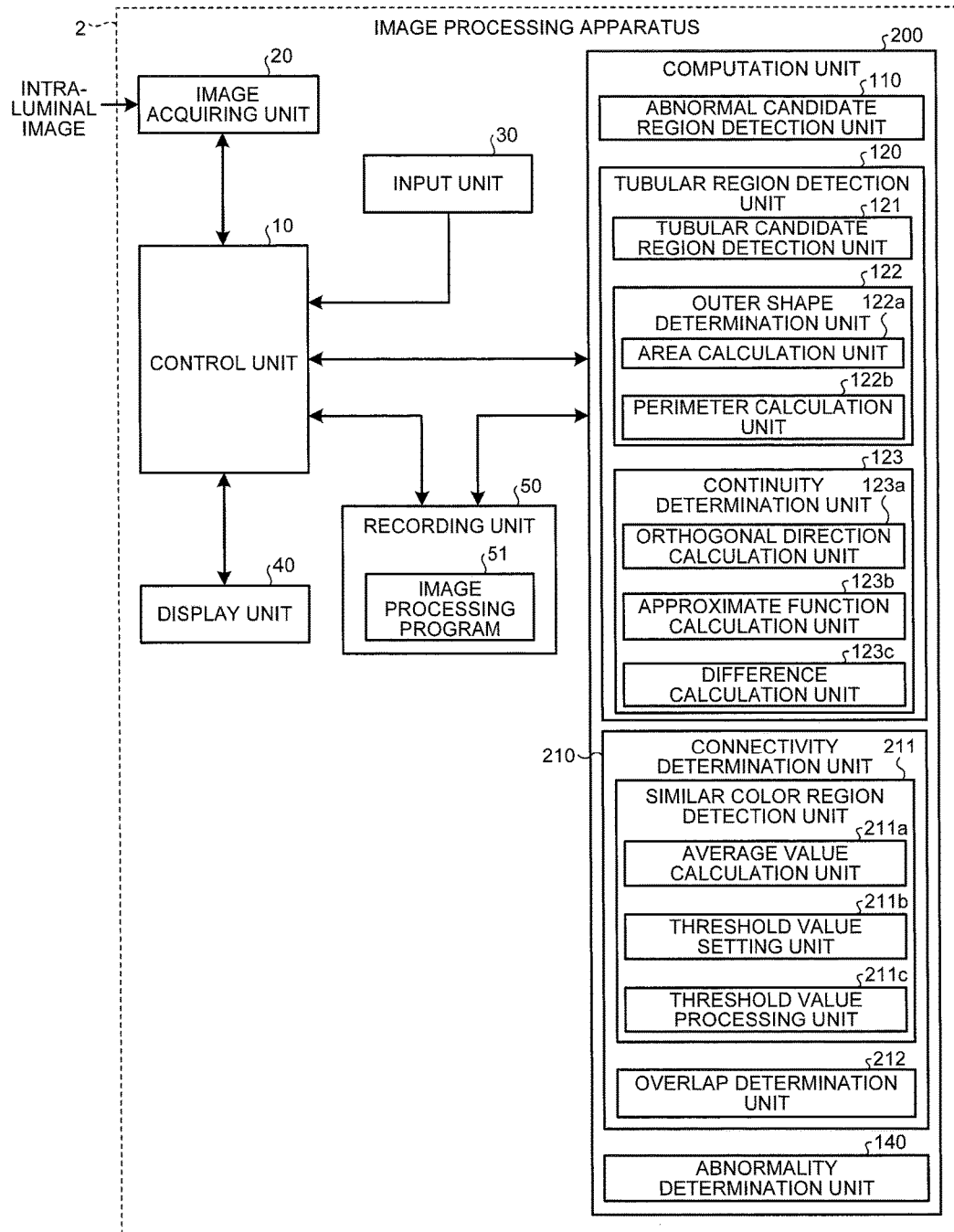
FIG. 12 is a block diagram illustrating a configuration of an image processing apparatus according to a second embodiment.

FIG. 12 is a block diagram illustrating a configuration of an image processing apparatus according to the second embodiment. As illustrated in FIG. 12, the image processing apparatus 2 according to the second embodiment includes a computation unit 200, instead of the computation unit 100 illustrated in FIG. 1.

The computation unit 200 includes a connectivity determination unit 210, instead of the connectivity determination unit 130 illustrated in FIG. 1. More specifically, the connectivity determination unit 210 has a similar color region detection unit 211 that detects a similar color region that has a color similar to that of a tubular region from an image, and an overlap determination unit 212 that determines an overlap (that is, duplication) of pixel positions in the abnormal candidate region and the tubular region with the similar color region. Of the foregoing components, the similar color region detection unit 211 includes an average value calculation unit 211a that calculates an average value of color feature data in the tubular region, a threshold value setting unit 211b that sets a threshold value based on the average value of color feature data, and a threshold value processing unit 211c that processes the image based on the threshold value set by the threshold value setting unit 211b. The components of the image processing apparatus 2 other than the connectivity determination unit 210 are the same as those illustrated in FIG. 1.

Next, operation of the image processing apparatus 2 will be described. The operation of the entire image processing apparatus 2 is the same as illustrated in FIG. 2, except that details of the process by the connectivity determination unit 210 (step S15) for determining connectivity between the abnormal candidate region and the blood vessel region are different from those of the first embodiment.

Figure 13:
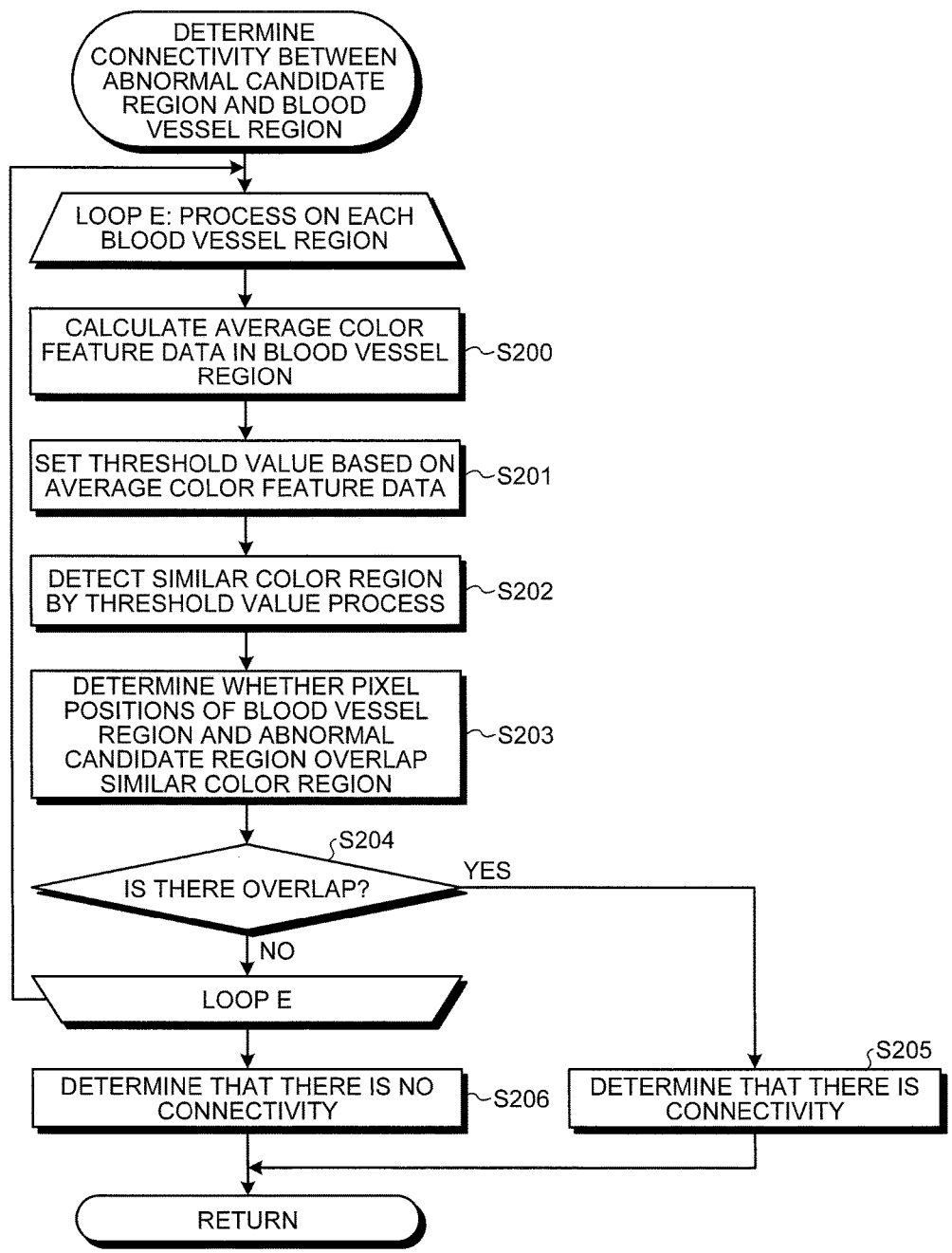
FIG. 13 is a flowchart of operation of the connectivity determination unit illustrated in FIG. 12.

FIG. 13 is a flowchart of detailed operation of the connectivity determination unit 210. The connectivity determination unit 210 performs a process of loop E on each of the blood vessel regions detected at step S12 (refer to FIG. 2).

First, at step S200, the average value calculation unit 211a calculates the average value of color feature data in the blood vessel region. In the second embodiment, G/R value is used as color feature data, and thus average G/R value is calculated at step S200.

At subsequent step S201, the threshold value setting unit 211b sets a threshold value based on the average color feature data calculated at step S200. Specifically, the threshold value setting unit 211b sets as a threshold value a value obtained by multiplying the average G/R value by an arbitrary coefficient α (α≥1).

At step S202, the threshold value processing unit 211c performs a threshold value process on the image to detect a region with a G/R value equal to or less than the threshold value, as a similar color region of the blood vessel region.

Further, at step S203, the overlap determination unit 212 determines whether both the blood vessel region and the abnormal candidate region overlap the similar color region (that is, whether at least some of the pixel positions in the blood vessel region overlap the similar color region and at least some of the pixel positions in the abnormal candidate region overlap the similar color region). Then, when both the blood vessel region and the abnormal candidate region overlap the similar color region (step S204: Yes), the connectivity determination unit 210 exits from the loop E and determines that the abnormal candidate region has connectivity with the blood vessel region (step S205). Meanwhile, when either one or both of the blood vessel region and the abnormal candidate region do not overlap the similar color region (step S204: No), the connectivity determination unit 210 repeats the process of loop E on another blood vessel region as a target of determination. Then, when the process is completely performed on all of the blood vessel regions, if no blood vessel region or abnormal candidate region overlapping the similar color region is detected, the connectivity determination unit 210 determines that the abnormal candidate region does not have connectivity with the blood vessel region (step S206). After that, the computation unit 200 returns operation to the main routine.

As described above, in the second embodiment, it is determined whether there is connectivity between an abnormal candidate region and a blood vessel region, by detecting a similar color region by a threshold value set based on color feature data in the blood vessel region and determining an overlap of pixel positions in the abnormal candidate region and the blood vessel region with the similar color region. Therefore, according to the second embodiment, it is possible to determine connectivity between the abnormal candidate region and the blood vessel region with higher accuracy, based on the color feature data in the blood vessel region.

The image processing apparatuses according to the first and second embodiments and the modified example can be realized by executing image processing programs recorded in a recording medium on a computer system such as a personal computer, a workstation, or the like. In addition, such computer system may be used in connection with devices such as other computer systems, servers, or the like, via a local area network or a wide area network (LAN/WAN), or a public line such as the Internet. In this case, the image processing apparatuses according to the first and second embodiments and the modified example may acquire image data in intraluminal images via the foregoing networks, output image processing results to various output devices (viewer, printer, or the like) connected via the foregoing networks, or store the image processing results in a recording device (recording device and reading device for the recording device or the like) connected via the foregoing networks.

The present invention is not limited to the first and second embodiments and the modified example but can be embodied in various forms by combining as appropriate a plurality of constituent elements disclosed in relation to the foregoing embodiments and modified example. For example, some of the constituent elements in the foregoing embodiments and modified example may be eliminated, or constituent elements in the different embodiments and modified example may be combined as appropriate.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a processor comprising hardware, wherein the processor is configured to:
detect an abnormal candidate region, as a candidate for an abnormal portion, from an intraluminal image obtained by capturing an image of an inside of a lumen of a subject;
detect a tubular region from the intraluminal image;
determine whether the abnormal candidate region and the tubular region are overlapped with each other at least in part;
in response to determining that the abnormal candidate region and the tubular region are not overlapped with each other at least in part, determine whether the abnormal candidate region and the tubular region are connected by a connecting region of a color similar to a color of the tubular region;
in response to determining that the abnormal candidate region and the tubular region are not connected by the connecting region of the color similar to the color of the tubular region, determine that the abnormal candidate region is the abnormal portion; and
in response to determining that the abnormal candidate region is the abnormal portion, control a display to display the abnormal portion.

2. The image processing apparatus according to claim 1, wherein the processor is configured to:
calculate inter-region feature data of the connecting region connecting the abnormal candidate region and the tubular region;
determine connectivity between the abnormal candidate region and the tubular region based on the inter-region feature data; and
determine whether the color of the connection region is similar to the color of the tubular region based on the connectivity between the abnormal candidate region and the tubular region.

3. The image processing apparatus according to claim 2, wherein the processor is configured to:
calculate an interpolation line between the abnormal candidate region and the tubular region; and
calculate feature data on the interpolation line as the inter-region feature data.

4. The image processing apparatus according to claim 3, wherein the processor is configured to calculate an edge strength on the interpolation line, that is, a maximum value of changes in pixel values between adjacent pixels or pixels at specified intervals therebetween on the interpolation line as the inter-region feature data.

5. The image processing apparatus according to claim 3, wherein the processor is configured to calculate a color edge strength on the interpolation line, that is, a maximum value of changes in color feature data between adjacent pixels or pixels at specified intervals therebetween on the interpolation line as the inter-region feature data.

6. The image processing apparatus according to claim 3, wherein the processor is configured to calculate an average value of color feature data on the interpolation line as the inter-region feature data.

7. The image processing apparatus according to claim 1, wherein the processor is configured to:
- detect a tubular candidate region as a candidate for the tubular region, based on color feature data in the intraluminal image; and
- determine whether the tubular candidate region is the tubular region based on continuity of pixel values in a surrounding region of the tubular candidate region.

8. The image processing apparatus according to claim 7, wherein the processor is configured to:
- calculate a direction orthogonal to a longitudinal direction of the tubular candidate region in a plane of the intraluminal image;
- calculate approximate functions for approximating changes in pixel values on both sides of the tubular candidate region in the orthogonal direction;
- calculate a difference between values of the approximate functions in a same coordinate in the orthogonal direction; and
- determine whether the tubular candidate region is tubular region based on the difference.

9. The image processing apparatus according to claim 1, wherein the processor is configured to:
- detect a tubular candidate region as a candidate for the tubular region, based on color feature data in the intraluminal image; and
- determine whether the tubular candidate region is the tubular region based on an outer shape of the tubular candidate region.

10. The image processing apparatus according to claim 9, wherein the processor is configured to:
- calculate an area of the tubular candidate region;
- calculate a perimeter of the tubular candidate region; and
- determine whether the tubular candidate region is the tubular region based on the area and the perimeter.

11. An image processing method comprising:
detecting an abnormal candidate region, as a candidate for an abnormal portion, from an intraluminal image obtained by capturing an image of an inside of an lumen of a subject;
detecting a tubular region from the intraluminal image;
determining whether the abnormal candidate region and the tubular region are overlapped with each other at least in part;
in response to determining that the abnormal candidate region and the tubular region are not overlapped with each other at least in part, determining whether the abnormal candidate region and the tubular region are connected by a connecting region of a color similar to a color of the tubular region;
in response to determining that the abnormal candidate region and the tubular region are not connected by the connecting region of the color similar to the color of the tubular region, determining that the abnormal candidate region is the abnormal portion; and
in response to determining that the abnormal candidate region is the abnormal portion, controlling a display to display the abnormal portion.

12. A computer-readable recording device with an executable program stored thereon, wherein the program instructs a processor to at least perform:
detecting an abnormal candidate region, as a candidate for an abnormal portion, from an intraluminal image obtained by capturing an image of an inside of a lumen of a subject;
detecting a tubular region from the intraluminal image;
determining whether the abnormal candidate region and the tubular region are overlapped with each other at least in part;
in response to determining that the abnormal candidate region and the tubular region are not overlapped with each other at least in part, determining whether the abnormal candidate region and the tubular region are connected by a connecting region of a color similar to a color of the tubular region;
in response to determining that the abnormal candidate region and the tubular region are not connected by the connecting region of the color similar to the color of the tubular region, determining that the abnormal candidate region is the abnormal portion; and
in response to determining that the abnormal candidate region is the abnormal portion, controlling a display to display the abnormal portion.

* * * * *